United States Patent [19]

Takano

[11] Patent Number: 4,855,495
[45] Date of Patent: * Aug. 8, 1989

[54] ENHANCED 2-HYDROXY-4-METHYLTHIOBUTANOIC ACID COMPOSITION AND METHOD OF PREPARATION

[75] Inventor: Masaharu Takano, St. Louis, Mo.

[73] Assignee: Monsanto Company, St. Louis, Mo.

[*] Notice: The portion of the term of this patent subsequent to Apr. 1, 2003 has been disclaimed.

[21] Appl. No.: 849,971

[22] Filed: Apr. 10, 1986

Related U.S. Application Data

[63] Continuation-in-part of Ser. No. 750,669, Jul. 2, 1985, which is a continuation-in-part of Ser. No. 529,191, Sep. 6, 1983, abandoned.

[51] Int. Cl.$^4$ ........................................... C07C 149/20
[52] U.S. Cl. .................................................... 562/581
[58] Field of Search ........................ 562/581; 514/557

[56] References Cited

U.S. PATENT DOCUMENTS

| | | | |
|---|---|---|---|
| 2,745,745 | 5/1956 | Blake et al. | 514/557 |
| 3,272,860 | 9/1966 | Nufer | 562/581 |
| 4,310,690 | 1/1982 | Cummins | 562/581 |
| 4,335,257 | 6/1982 | Cummins et al. | 562/581 |
| 4,353,924 | 10/1982 | Baker et al. | 514/557 |
| 4,579,962 | 4/1986 | Takano | 562/581 |

FOREIGN PATENT DOCUMENTS 49057 4/1982 European Pat. Off. ............ 562/581

Primary Examiner—Bruce Gray
Attorney, Agent, or Firm—Jon H. Beusen; Dennis R. Hoerner, Jr.; George R. Beck

[57] ABSTRACT

An enhanced 2-hydroxy-4-methylthiobutanoic acid composition and method of preparation are disclosed. The enhanced composition comprises greater than 2.2 and less than about 10 moles of 2-hydroxy-4-methylthiobutanoic acid equivalent per mole of calcium.

6 Claims, No Drawings

ENHANCED 2-HYDROXY-4-METHYLTHIOBUTANOIC ACID COMPOSITION AND METHOD OF PREPARATION

BACKGROUND OF THE INVENTION

This is a continuation-in-part of application Ser. No. 750,669, filed July 2, 1985, which is a continuation-in-part of application Ser. No. 529,191 filed Sept. 6, 1983, now abandoned.

The present invention relates to 2-hydroxy-4-methylthiobutanoic acid, an analogue of the essential amino acid methionine, commonly referred to as methionine hydroxy analogue. More particularly, the present invention relates to solid methionine hydroxy analogue compositions which have a substantially higher 2-hydroxy-4-methylthiobutanoic acid content than solid compositions reported heretofore.

Various methods for preparing methionine are known. For example, the synthesis of methionine from methyl mercaptan and acrolein involves the preparation of methylmercaptopropionaldehyde which is reacted with hydrocyanic acid to form 2-hydroxy-4-methylthiobutyronitrile which is subsequently aminated and hydrolyzed to methionine. Unfortunately, the reaction of 2-hydroxy-4-methylthiobutyronitrile with ammonia is a difficult and costly procedure requiring the use of high pressure apparatus. It was subsequently found that methionine analogues such as 2-hydroxy-4-methylthiobutanoic acid, hereinafter referred to as HMBA, are virtually as effective as methionine for nutritional uses, particularly as a poultry feed supplement. However, the crystalline form of HMBA has a melting point between 38° C. and 42° C. depending on the purity, rendering it susceptible to liquid-solid phase change upon storage or use at ambient temperatures. Since all feed milling operations, particularly those in developing countries, are not equipped to handle liquids in their mixing processes, a stable, solid form of HMBA is often more practical.

A solid form of HMBA has been disclosed wherein the acid is sprayed onto a solid support such as feed grade vermiculite, for example see Romoser et al., *Poult. Sci.* 55 (3), pp 1099-1103 (1976). Unfortunately, at the high loadings necessary to achieve reasonable methionine activity per unit weight the composition often becomes sticky, does not flow freely and is highly hygroscopic.

While various salts of 2-hydroxy-4methylthiobutanoic acid have been disclosed, only the calcium salt of HMBA is approved by the United States Food and Drug Administration for use as an animal feed supplement. The conventional calcium salt of HMBA, hereinafter referred to as Ca(HMBA)$_2$, consists of two moles of HMBA equivalent per mole of calcium. The conventional calcium salt of HMBA decomposes at a temperature above 245° C. without melting. Moreover, methods disclosed for preparing the above-described calcium salt teach reacting essentially stoichiometric amounts of 2-hydroxy-4-methylthiobutanoic acid and calcium oxide or calcium hydroxide to yield the conventional ionic salt, for example see U. S. Pat. No. 4,335,257.

It is therefore the overall object of the present invention to provide a solid form of HMBA having substantially higher HMBA equivalent per unit weight than solid forms disclosed heretofore.

It is an object of the present invention to provide a solid form of HMBA which flows freely and is not highly hygroscopic.

It is another object of the present invention to provide a calcium salt complex of HMBA having substantially higher HMBA equivalent than the conventional calcium salt disclosed heretofore.

It is yet another object of the present invention to provide a process for preparing the enhanced HMBA compositions embraced by the present invention.

These and other objects, features and advantages of the present invention will become evident to those skilled in the art from the following description.

SUMMARY OF THE INVENTION

The present invention provides enhanced 2-hydroxy-4-methylthiobutanoic acid compositions comprising greater than two and less than about ten moles of HMBA equivalent per mole of calcium. Compositions comprising less than about six moles of HMBA equivalent per mole of calcium are preferred since these compositions made by the process of this invention are free flowing powders or agglomerates and therefore possesses superior blending characteristics.

The composition can be easily prepared by reacting HMBA with the conventional calcium salt or by contacting calcium oxide, hydroxide or carbonate with HMBA in the presence or absence of a heel of the conventional calcium salt of HMBA or the enhanced HMBA composition of the present invention. Alternately, compositions comprising greater than two and less than about four moles of HMBA equivalent per mole of calcium can be easily formed by crystallization from an aqueous solution of HMBA and Ca(HMBA)$_2$, calcium oxide or calcium hydroxide.

DETAILED DESCRIPTION OF THE INVENTION

It has been found that when the calcium salt of 2-hydroxy-4-methylthiobutanoic acid is crystallized from aqueous solution in the presence of an excess of HMBA a salt complex is formed. The salt complex has a distinctly different crystalline structure than Ca(HMBA)$_2$ as evidenced by X-ray powder diffraction. While not fully understood, the salt complex embraced by the present invention consists of about four moles of HMBA per mole of calcium (hereinafter represented by the formula Ca(HMBA)$_4$) and has a melting point of about 130° C.

While Ca(HMBA)$_2$ consists of approximately 88.8 wt % HMBA equivalent, the salt complex of the present invention (Ca(HMBA)$_4$) consists of approximately 94.0 wt % HMBA equivalent. It should therefore be evident to one skilled in the art that preparation and use of the enhanced HMBA compositions of the present invention affords numerous advantages over the conventional calcium salt as a methionine activity source in animal rations. The enhanced compositions have greater methionine activity per unit weight, lower manufacturing cost per unit methionine activity and requires less storage space per unit methionine activity.

The structural difference between the conventional calcium salt (Ca(HMBA)$_2$) and the salt complex (Ca(HMBA)$_4$) is indicated by the difference in their respective X-ray diffraction patterns. Unless otherwise noted, all X-ray diffraction scans were done with a wavelength of 1.54 angstroms using a CuK$\alpha$ X-ray source at 45 kilovolts peak/40 milliamperes. Referring to the table below, the d-spacing (d) and relative intensity ($I/I_o$) of the ten strongest diffraction peaks are compared for Ca(HMBA)$_2$ and the salt complex. The strongest diffraction from 16.45 Å spacing which is unique for the conventional calcium salt disappears in the salt complex. Moreover, the diffraction peaks for the salt complex are very broad indicating a less ordered cyrtalline structure.

|  | Peak No. | d(Å) | $I/I_o$ |
|---|---|---|---|
| Conventional Salt Ca(HMBA)$_2$ | 1 | 16.45 | >>100 |
|  | 2 | 8.23 | 85 |
|  | 3 | 7.92 | 20 |
|  | 4 | 7.58 | 15 |
|  | 5 | 5.49 | 60 |
|  | 6 | 4.56 | 15 |
|  | 7 | 4.45 | 100 |
|  | 8 | 4.38[1] | 50 |
|  | 9 | 4.21 | 15 |
|  | 10 | 4.12 | 90 |
| Salt Complex Ca(HMBA)$_4$ - Example 6 | 1 | 38.3[2] | 10 |
|  | 2 | 15.7[2] | 100 |
|  | 3 | 9.78[2] | 10 |
|  | 4 | 7.79[2] | 10 |
|  | 5 | 6.85[2] | 10 |
|  | 6 | 4.81[2] | 13 |
|  | 7 | 4.46[2] | 65 |
|  | 8 | 3.95[2] | 30 |
|  | 9 | 2.63[2] | 3 |
|  | 10 | 2.35[2] | 3 |

[1]doublet peak
[2]very broad peak

While the present invention embraces the formation of the above-described salt complex, the present invention contemplates in its broadest aspects the discovery that enhanced HMBA compositions can be prepared in solid form which comprise greater than two moles and less than about ten moles of HMBA equivalent per mole of calcium. Moreover, the excess free HMBA is present in essentially monomeric form as determined by gas chromatographic analysis. The enhanced HMBA compositions of the present invention first exhibit solid/liquid phase change at a temperature substantially above that observed for free crystalline HMBA. More particularly, the enhanced HMBA compositions of the present invention first exhibit solid/liquid phase change at temperatures above about 100° C. Compositions consisting of four or more moles of HMBA equivalent per mole of calcium exhibit complete melting at temperatures of about 140° C.

While not fully understood, compositions comprising less than four moles of HMBA equivalent per mole of calcium are believed to exist as a mixture of conventional calcium salt made up of 2 moles of HMBA equivalent per mole of calcium and the abovedescribed complex. Compositions comprising a mixture of Ca(HMBA)$_2$ and Ca(HMBA)$_4$ only partially melt at the salt complex melting temperature of about 130° C. and decompose at temperatures of between 180° and 245° C. without completely melting.

When more than four moles of HMBA are used per mole of calcium, the excess free HMBA is believed to make a sort of alloy with the salt complex crystals. Compositions comprising less than about six moles of HMBA equivalent per mole of calcium are preferred since these compositions prepared by the process described hereinafter are free flowing powders or agglomerates and therefore possess superior blending characteristics.

The X-ray diffraction data for compositions consisting of six and eight moles of HMBA equivalent per mole of calcium are listed in the table below. Increasing the molar ratio of HMBA equivalent to calcium decreases the peak intensity for d-spacings in the 4 Å range. The stronger peaks also shift to smaller d-spacings on the other end of the scan spectrum. These changes indicate that the compositions become more amorphous with increased HMBA content.

|  | Peak No. | d(Å) | $I/I_o$ |
|---|---|---|---|
| Ca(HMBA)$_6$[1] | 1 | 15.5 | 100 |
|  | 2 | 12.6 | 15 |
|  | 3 | 4.88 | 25 |
|  | 4 | 4.45[3] | 30 |
|  | 5 | 3.94[3] | 10 |
|  | 6 | 3.48 | 2 |
|  | 7 | 2.84 | 5 |
| Ca(HMBA)$_8$[2] | 1 | 17.9 | 20 |
|  | 2 | 14.2 | 25 |
|  | 3 | 12.7 | 100 |
|  | 4 | 8.94 | 9 |
|  | 5 | 7.10 | 10 |
|  | 6 | 5.23 | 9 |
|  | 7 | 4.73 | 13 |
|  | 8 | 4.24[4] | 8 |
|  | 9 | 3.65 | 9 |
|  | 10 | 3.61[4] | 12 |

[1]composition of Example 12
[2]composition of Example 12
[3]very broad peak
[4]doublet peak The usual commercial form of HMBA is the optically inactive, racemic D,L-HMBA mixture. It should be understood that while the HMBA compositions referred to hereinafter are racemic mixtures, the individual D- and L- isomers of HMBA can be converted to the enhanced solid HMBA compositions of the present inventions by the procedures described hereinafter. Hence, for purposes of the present invention by "HMBA" is meant either the D- or L- isomer of 2-hydroxy-4-methylthiobutanoic acid or any mixture of the two above-described isomers thereof.

By "HMBA equivalent" is meant the amount of free HMBA which correspond to the HMBA present in the composition whether in free acid or ionized form. For example, while not fully understood, compositions comprising four moles of HMBA equivalent per mole of calcium are believed to comprise two moles of free acid and two moles of ionized HMBA per mole of calcium.

The enhanced HMBA compositions of the present invention are preferably prepared by reacting calcium hydroxide or calcium oxide with more than stoichiometric amounts of HMBA. When four moles of HMBA are reacted at room temperature with one mole of Ca(OH)$_2$ or CaO, a loosely structured complex is formed. When more than four moles of HMBA are reacted with one mole of Ca(OH)$_2$ or CaO, more loosely structured complexes are formed. The compositions gradually become amorphous as the molar ratio of HMBA to calcium increases above four. Water can be easily removed by heating the enhanced HMBA compositions above about 70° C.

Compositions of the present invention can also be prepared by reacting one mole of calcium oxide, hydroxide or carbonate with more than two moles of HMBA (neat or in aqueous solution) in the presence or absence of a heel of the conventional calcium salt of HMBA or the enhanced salt complex of the present invention above 70° C. While it should be understood that the presence of a heel of the enhanced salt complex or Ca(HMBA)$_2$ is not critical to the present invention, the presence of a heel renders the mixture less sticky and easier to admix to substantial homogeneity. If a heel is used, it is preferred that the heel comprise at least 20 percent of the total mass of the mixture. It should be further understood that while temperature is not a critical parameter to the present invention, the enhanced HMBA compositions melt above 130° C. The enhanced HMBA compositions prepared with high shear (rapid mixing) at temperatures about 70° C. are highly crystalline, and show a distinctly different X-ray diffraction pattern from those for the conventional calcium salt of HMBA and the enhanced salt complex prepared without shear.

When one mole of calcium hydroxide powder is reacted with two moles of HMBA in its aqueous 88% solution at temperature above 70° C. in the presence of high shear, the resulting powdery product shows an X-ray powder diffraction pattern which is virtually identical with that of the conventional calcium salt crystallized from a diluted aqueous slurry of calcium hydroxide and HMBA and dried above 70° C.

When the molar ratio of HMBA equivalent to calcium is smaller than four, the presence of Ca(HMBA)$_2$ is still recognized.

When the molar ratio of HMBA equivalent to calcium is four, a highly crystalline material is obtained which exhibits an X-ray powder diffraction pattern very different from those of the conventional calcium salt, Ca(HMBA)$_2$ and the same composition crystallized without shear. The diffraction peaks from various spacings are also very sharp, compared with the very broad diffraction peaks observed for the latter.

| | Peak No. | d(Å) | I/I$_o$ |
|---|---|---|---|
| Ca(HMBA)$_2$ | 1 | 16.5 | >>100 |
| | 2 | 9.13 | 15 |
| | 3 | 8.25 | 70 |
| | 4 | 5.5 | 25 |
| | 5 | 4.56 | 20 |
| | 6 | 4.46 | 100 |
| | 7 | 4.39[1] | 50 |
| | 8 | 4.13 | 80 |
| | 9 | 3.96[1] | 15 |
| | 10 | 3.48 | 15 |
| Ca(HMBA)$_{2.6}$ | 1 | 16.4 | >>100 |
| (Example 2) | 2 | 8.24 | 85 |
| | 3 | 7.94 | 20 |
| | 4 | 5.50 | 30 |
| | 5 | 4.61 | 20 |
| | 6 | 4.57 | 25 |
| | 7 | 4.46 | 100 |
| | 8 | 4.38[1] | 50 |
| | 9 | 4.12[1] | 95 |
| | 10 | 3.48 | 25 |
| Ca(HMBA)$_4$ | 1 | 17.8 | 40 |
| (Example 1) | 2 | 16.5 | 100 |
| | 3 | 14.2 | 30 |
| | 4 | 12.6 | 70 |
| | 5 | 10 | 15 |
| | 6 | 8.93 | 15 |
| | 7 | 5.52 | 15 |
| | 8 | 4.72 | 10 |
| | 9 | 4.11 | 15 |
| | 10 | 4.00[1] | 15 |

[1]doublet peak

Finally, enhanced HMBA compositions comprising greater than two and less than about four moles of HMBA equivalent per mole of calcium can be crystallized from an aqueous solution comprising HMBA and Ca(HMBA)$_2$, calcium oxide or calcium hydroxide. For example, the enhanced salt complex comprising about four moles of HMBA equivalent per mole of calcium can be crystallized from an aqueous solution comprising between about 2.5 and 3.0 moles of HMBA per mole of Ca(HMBA)$_2$. The reactants are preferably dissolved at a temperature above about 70° C. and then slowly cooled to room temperature. Drying the product composition at temperatures above about 70° C. frees the water of hydration and produces essentially fine crystals. Gas chromatographic analysis of the salt complex composition crystallized indicates that the excess free HMBA included in the salt complex is essentially in monomeric form.

The following examples are included to better illustrate the practice of the present invention. It should be understood that these examples are included for illustrative purposes only and are not, in any way, intended to limit the scope of the present invention. While preparation of the enhanced HMBA compositions is described hereinafter with reference to batch operations, it is evident to those skilled in the art that continuous processing is also suitable for practice of the present invention. Although the aqueous solutions used hereinafter are fairly concentrated, the amount of water present in the process of the present invention should not be considered critical, but rather a matter of economics since water remaining in wet products must be evaporated off to obtain a free flowing, powdery product. Unless otherwise noted, all percentages are by weight and all temperatures are in degrees centigrade.

EXAMPLE 1

A batch operation was performed in a laboratory-scale double arm, sigma blade mixer. The mixing chamber was open to the atmosphere in a laboratory hood. A 372.3 gm sample of Ca(HMBA)$_2$ was warmed to 85° C. with low pressure steam in the jacket of the mixer. Four portions (93.3 gm., 92.6 gm., 94.5 gm. and 96.3 gm.) of an aqueous 88% HMBA solution were uniformly added to the mixer from a beaker at about fifteen minute intervals. The composition was almost dry within fifteen minutes of each HMBA addition. The composition was further mixed and dried in the laboratory mixer for twenty-seven minutes at 73°–82° C. following the last HMBA addition. A 634.8 gm mass of product was recovered from the mixer. Subsequent loss on drying at 70° C. overnight was approximately 0.4 wt %. Analysis of the dry powdery product by X-ray powder diffraction showed a highly crystalline structure which was distinctly different from Ca(HMBA)$_2$. The enhanced salt complex and Ca (HMBA)$_2$ content of the dry product were estimated to be greater than 90 wt % and less than 10 wt %, respectively by X-ray powder diffraction and gas chromatographic determination of the free HMBA monomer content of the product. The product composition exhibited initial melting at about 128° C. and completely melted at about 131° C.

EXAMPLE 2

A 284.5 gm heel of Ca(HMBA)$_2$ and 27.8 gms of calcium hydroxide were mixed and warmed to 78° C. as described in Example 1. A 256.1 gm sample of an aqueous 88% HMBA solution as described above was added to the mixer chamber over a five minute period at 78°–86° C. The resulting composition was mixed and dried in the mixer at 74°–82° C. for about thirty seven minutes. The partially dried product was further dried overnight at 70° C.

Analysis of the dried product indicated an HMBA equivalent of 91.8 wt %. The enhanced salt complex and Ca(HMBA)$_2$ content of the dry product were estimated to be about 42 wt % and 58 wt %, respectively, by X-ray powder diffraction and gas chromatographic determination of the free HMBA monomer content of the product. The product composition exhibited initial melting at about 127° C. and decomposed at about 245° C. without completely melting. The presence of Ca(HMBA)$_2$ is indicated by the X-ray diffraction pattern.

EXAMPLE 3

Calcium hydroxide and an aqueous 88% HMBA solution were mixed in various proportions in evaporating dishes at room temperature (22° C.) using a metal spatula. The product compositions were either wet powder, dough-like material, or paste depending on the reactant proportions. After being dried overnight at 70° C. and then ground all product compositions became free flowing powders. Analytical results of product compositions comprising greater than two and up to about four moles of HMBA equivalent per mole of calcium are summarized as follows:

| Composition | I | II | III | IV | V | VI |
|---|---|---|---|---|---|---|
| 88% HMBA, gm. | 16.8 | 16.8 | 16.8 | 16.8 | 16.8 | 16.8 |
| Ca(OH)$_2$, gm. | 3.7 | 3.3 | 3.0 | 2.6 | 2.2 | 1.8 |
| Molar Ratio, HMBA/Ca(OH)$_2$ | 2.0 | 2.2 | 2.5 | 2.9 | 3.3 | 4.0 |
| Product, wt % | | | | | | |
| HMBA equiv. | 86.9 | 87.1 | 89.3 | 90.8 | 90.6 | 93.2 |
| Water, wt % | 0.0 | 2.2 | 2.5 | 1.2 | 0.9 | 1.5 |

It should be noted that compositions comprising salt complex and Ca(HMBA)$_2$ prepared at low temperatures (22°-70° C.) tend to form hydrates. It should be further noted, however, that the hydrates may be freed of water of hydration by drying the compositions at temperatures above about 70° C. Compositions consisting of between 2.2 and 2.9 moles of HMBA per mole of calcium exhibited initial melting at a temperature of about 130° C. and decomposed at about 245° C. without completely melting. Compositions consisting of 3.3 and 4.0 moles of HMBA per mole of calcium exhibited melting between about 122° C. and 138° C.

EXAMPLE 4

A 34.1 gm sample of an aqueous 88% HMBA solution was mixed with 3.71 gms of calcium hydroxide in an evaporating dish at room temperature (22° C.) and dried overnight at 22° C. When the moisture content had reached 11 wt %, the product composition was extruded through 16 mesh metal screen to produce a granular product. After drying overnight at 70° C. the extrudate was a hard, dried spaghetti-like material. The total HMBA equivalent content was 94.7 wt %. The product composition exhibited initial melting at about 124° C. and completely melted at a temperature of about 132° C.

EXAMPLE 5

A 34.1 gm sample of an aqueous 88% HMBA solution was mixed with 2.80 gms of calcium oxide in an evaporating dish at room temperature (22° C.) and dried overnight 22° C. When the moisture content had reached 10 wt %, the product composition was extruded through a 16 mesh metal screen to produce a granular product. After drying overnight at 70° C., the extrudate was a hard, dried spaghetti-like material. Total HMBA equivalent content was 95.3 wt %. The product composition exhibited initial melting at about 123° C. and completely melted at a temperature of about 132° C.

EXAMPLE 6

A 92.4 gm sample of Ca(HMBA)$_2$ (HMBA equivalent 87.09 wt %) and 114.6 gms of an aqueous 88% HMBA solution were mixed in 343.8 gms of water and warmed to 92° C. The solid particles were filtered out and the filtrate permitted to cool. Upon slow cooling overnight at room temperature (22° C.) the filtrate yielded a large quantity of precipitate. Analysis of product crystals after drying overnight at 70° C. indicated a total HMBA equivalent of 93.5 wt %. The dried product was a free flowing powder.

Under microscopic examination, the crystals of salt complex appeared as shiny glassy material while conventional Ca(HMBA)$_2$ crystals appeared as white powder. The product composition exhibited initial melting at about 133° C. and completely melted at a temperature of about 138° C.

EXAMPLE 7

A 156.9 gm heel of Ca(HMBA)$_2$ and 28.9 gms of calcium oxide were mixed and warmed to 88° C. in a laboratory-scale double arm, sigma blade mixer. A 337.6 gm aliquot of an aqueous 89 wt % HMBA solution was slowly added to the mixer chamber over a seventy-three minute period. Moisture was evaporated off over an additional eighteen minute period.

Analysis of the product without further drying indicated an HMBA equivalent content of 92.4 wt %. The product composition exhibited initial melting at a temperature of about 123° C. and decomposed at about 183° C. without completely melting.

EXAMPLE 8

A 113.5 gm heel of Ca(HMBA)$_2$ and 25.5 gms of calcium hydroxide were mixed and warmed to 81° C. in a preheated laboratory-scale double arm sigma blade mixer. A 428.5 gm sample of an aqueous 70 wt % HMBA solution was slowly added to the mixer chamber over a one hundred thirty-six minute period. Moisture was evaporated off over an additional twenty-five minute period.

Analysis of the product without further drying indicated an HMBA equivalent content of 94.0 wt %. The product composition exhibited initial melting at about 122° C. and completely melted at a temperature of about 132° C.

EXAMPLE 9

A 180.4 gm aliquot of a 98 wt % HMBA solution was slowly added to a 200.0 gm sample of Ca(HMBA)$_2$ in a laboratory-scale planetary mixer at 25° C.

Analysis of the undried product indicated a HMBA equivalent content of 92.1 wt %. The product composition exhibited initial melting at a temperature of about 113° C. and completely melted at a temperature of about 123° C.

EXAMPLE 10

A 38.2 gm sample of calcium hydroxide was mixed with a 93.8 gm heel of enhanced salt complex comprising about four moles of HMBA equivalent per mole of calcium in a laboratory-scale sigma blade mixer preheated to 72° C. A 338.2 gm sample of an aqueous 89 wt % HMBA solution was slowly added to the mixture over a seventy-five minute period. Moisture was evaporated off over an additional fifteen minuted period.

Analysis of the product without further drying indicated an HMBA equivalent content of 94.3 wt %. The product composition exhibited initial melting at a temperature of about 119° C. and decomposed at about 187° C. without completely melting.

EXAMPLE 11

Calcium hydroxide was mixed with varying concentrations of an aqueous HMBA solution so that in each case calcium and HMBA were present in a one to four molar ratio. The HMBA solutions used ranged from 50.9 to 99.8 wt % HMBA. The compositions were mixed in evaporating dishes at room temperature (22° C.) using a metal spatula. Products were either dough-like material or paste depending on the amount of water involved. However, after being dried overnight at 70° C. and then ground all product compositions were free flowing powders. All dried product compositions exhibited an angle of repose of approximately 40 degrees. The product compositions exhibited initial melting at a temperature as low as 107° C. All compositions were completely melted at a temperature of about 133° C.

EXAMPLE 12

Calcium hydroxide and an aqueous 88 wt % HMBA solution were mixed in various proportions so as to attain mixtures crrresponding to between 4 and 10 moles (at integral increments, inclusive) of HMBA equivalent per mole of calcium. The compositions were mixed in evaporating dishes at room temperature (22° C.) using a metal spatula. The product compositions varied from dough-like material to paste depending on reactant concentrations. After being dried overnight at 70° C. and then ground, compositions comprising four to six moles of HMBA equivalent per mole of calcium were free flowing powders with an angle of repose of about 40 degrees. Compositions comprising seven to ten moles of HMBA equivalent per mole of calcium were tacky to sticky materials with an angle of repose between about fifty and eighty-five degrees. Product compositions exhibited initial melting at temperatures as low as 105° C. All compositions were completely melted at a temperature of about 135° C. The X-ray powder diffraction patterns of 6:1 and 8:1 compositions show that the compositions are not as highly crystalline as the conventional salt, but do exhibit a loose crystalline structure. The structure becomes more amorphous as the molar ratio of HMBA equivalent to calcium increases.

I claim:

1. A solid composition consisting essentially of calcium and 2-hydroxy-4-(methylthio)butanoic acid equivalent (HMBA), said composition having an HMBA/calcium molar ratio greater than 2.2 and less than 10 and first exhibitinq solid/liquid phase change at a temperature a above 100° C. and comprising Ca(HMBA)$_4$ salt complex.

2. A composition of claim 1 in which said HMBA/calcium molar ratio is greater than 4 and less than about 6.

3. The composition of claim 1 in which said HMBA/calcium molar ratio is about 4 and exhibits a melting point at above 130° C.

4. A method for preparing enhanced 2-hydroxy-4-(methylthio)butanoic acid compositions which comprises reacting the conventional calcium salt of 2-hydroxy-4-(methylthio)butanoic acid with 2-hydroxy-4-(methylthio)butanoic acid so that the overall content of the mixture comprises greater than 2.2 and less than 10 moles of 2-hydroxy-4-(methylthio)butanoic acid equivalent (HMB.A) per mole of calcium to produce a composition comprising Ca(HMBA)$_4$ salt complex.

5. A method for preparing enhanced 2-hydroxy-4-(methylthio)butanoic acid compositions which comprises reacting 2-hydroxy-4-(methylthio)butanoic acid with a calcium source selected from the group consisting of calcium oxide, calcium hydroxide and calcium carbonate so that the overall content of the mixture comprises greater than 2.2 and less than about 10 moles of 2-hydroxy-4-(methylthio)butanoic acid equivalent (HMBA) per mole of calcium to produce a composition comprising Ca(HMBA)$_4$ salt complex.

6. A method of claim 5 in which the reaction is carried out at a temperature of about 70° C. or above.

* * * * *